United States Patent [19]

Wall

[11] Patent Number: 4,922,747
[45] Date of Patent: May 8, 1990

[54] METHOD FOR THE DETERMINATION OF VOLATIVE COMPONENTS IN CONTINUOUS FLOW CONDENSED PHASE SAMPLE STREAM

[75] Inventor: David L. Wall, Burlington, Mass.

[73] Assignee: Spectra-Physics, Inc., San Jose, Calif.

[21] Appl. No.: 312,644

[22] Filed: Feb. 17, 1989

[51] Int. Cl.$^5$ ............................................ G01N 33/28
[52] U.S. Cl. ................................ 73/61.1 R; 73/61 R; 73/19
[58] Field of Search ................. 73/61 R, 61.1 R, 61.3, 73/19

[56] References Cited

U.S. PATENT DOCUMENTS

| | | | |
|---|---|---|---|
| 2,741,911 | 4/1956 | Fitzpatrick et al. | 73/19 |
| 3,885,930 | 5/1975 | Scheerer | 73/61 R X |
| 3,926,038 | 12/1975 | Wunning et al. | 73/61.3 X |
| 3,942,356 | 3/1976 | Branscombe et al. | 73/61 R X |
| 3,960,523 | 6/1976 | Ryan | 73/61 R X |
| 4,068,953 | 1/1978 | Harney et al. | 356/75 |
| 4,156,571 | 5/1979 | Ljung | 356/445 |
| 4,196,402 | 4/1980 | Butler et al. | 331/94.5 |
| 4,242,584 | 12/1980 | Krieg et al. | 250/423 |
| 4,248,599 | 2/1981 | Mommessin et al. | 23/230 |
| 4,257,257 | 3/1981 | Dairaku et al. | 73/19 |
| 4,272,734 | 6/1981 | Jarrett et al. | 331/94.5 |
| 4,381,923 | 5/1983 | Wada | 23/293 |
| 4,410,273 | 10/1983 | Mantz et al. | 356/319 |
| 4,462,686 | 7/1984 | Bridges | 356/318 |
| 4,480,039 | 10/1984 | Closmann et al. | 436/175 |
| 4,499,752 | 2/1985 | Fruzzetti et al. | 73/40.7 |
| 4,634,864 | 1/1987 | Lucatorto et al. | 250/282 |
| 4,745,795 | 5/1988 | Emmert | 73/61 R X |

OTHER PUBLICATIONS

Dual Beam, Second Derivative Tunable Diode Laser Infrared Spectroscopy Applied to Trace Gas Measurement; David R. Tallant, Rudolph G. Jungst, Sandia National Laboratories.
Standard Addition Technique for Quantitative Trace Gas Analysis Using Derivative Infrared Diode Laser Spectroscopy; John A. Mucha, Applied Spectroscopy, vol. 36, No. 4, 1982.
Calibration of Diode-Laser Second-Derivative Modulation Spectrometry with a Reference Cell; Claus Weitkamp, Applied Optics, vol. 23, No. 1, 1 Jan., 1984.
High Sensitivity Pollution Detection Employing Tunable Diode Lasers; J. Reid, J. Shewchun, B. K. Garside, and E. A. Ballik; Applied Optics, vol. 17, No. 2, 15 Jan., 1978.
Tunable Diode Laser Spectroscopy; an invited review; R. S. Eng, J. F. Butler, K. J. Linden, Optical Engineering, vol. 16, No. 6, Nov./Dec. 1980.
SP5100 Isotope Ratio Measurement System; D. L. Wall, R. S. Eng & A. W. Mantz; Spectra-Physics, Laser Analytics Division.
Second Derivative Tunable Diode Laser Spectrometry for Line Profile Determination. II. Experimental Results; David L. Grieble, Mark L. Olson, Jeffrey N. P. Sun & Peter R. Griffiths, Applied Spectroscopy, vol. 34, No. 1, 1980.

Primary Examiner—Hezron E. Williams
Assistant Examiner—Joseph W. Roskos
Attorney, Agent, or Firm—Allegretti & Witcoff, Ltd.

[57] ABSTRACT

A method for determining volative components in a continuous flow condensed phase sample stream. A method is disclosed wherein a controlled flow of a sample stream of oil is cascaded down a standpipe of a predetermined length and a countercurrent flow of an inert dry gas is created to absorb volatile substances, such as water, in a concentration proportional to the concentration in the oil. The cascade of oil down the standpipe creates an efficient mechanism for the transfer of volatiles from the oil to a gas phase with the inert gas. The inert gas exposed to and containing the volatiles is applied to a detection system for the measurement of the concentration of the volatiles.

16 Claims, 2 Drawing Sheets

4,922,747

METHOD FOR THE DETERMINATION OF VOLATIVE COMPONENTS IN CONTINUOUS FLOW CONDENSED PHASE SAMPLE STREAM

FIELD AND BACKGROUND OF THE INVENTION

The present invention relates to the detection of water in oil. The online production of crude oil requires the detection of water content in the oil on an online basis. The water is typically present in very minute or trace quantities and its detection is difficult to accurately measure, particularly in an online context.

The detection of volatiles such as water in oil is attempted in the prior art by causing the volatile to evaporate to the gas phase. The transfer of volatile substances like water from a fluid mixture to a gas phase for detection involves many parameters that affect the efficiency of transfer and can thus alter the concentration of the volatile in the gas phase which in turn can vary the accuracy of any measurement of the volatile based upon the detection of the vapor phase concentration as a measure of volatile in the oil.

SUMMARY OF THE INVENTION

The present invention provides for accurate online measurement of water, or other volatiles, in oil by cascading a controlled flow of a sample stream of the oil down a standpipe of predetermined length and creating a countercurrent flow of an inert dry gas to absorb the volatile substance in a concentration proportional to the concentration in the oil. The standpipe is contained within a column that provides a conduit for the countercurrent flow of the inert gas, typically nitrogen. The cascade of oil down the standpipe creates an efficient mechanism for the transfer of volatiles like water from the oil to a gas phase with the inert gas. A consistency in the efficiency of transfer of the water from the oil to the inert gas is ensured by operating the gas and oil flow at controlled rates and operating so as to avoid saturation of the water vapor in the inert gas as it exhausts the column.

The inert gas exposed to and containing the water vapor is applied to a detection system for the measurement of the concentration of the water vapor. In the preferred embodiment, this is accomplished by detecting laser radiation absorption in a cell containing the inert gas and water vapor combination. To this end the inert gas is flowed through a sample cell to which a modulated laser beam from a diode laser is applied. The intensity of the beam passing through is detected and processed so as to evaluate the intensity. The same measurement is made on a reference cell of a predetermined concentration of water vapor in the inert gas. The system is calibrated with a range of predetermined concentrations of water in oil.

DESCRIPTION OF THE DRAWING

These and other features of the invention are more fully set forth below in the solely exemplary detailed description and the accompanying drawing of which.

DETAILED DESCRIPTION OF THE INVENTION

Figure 1:
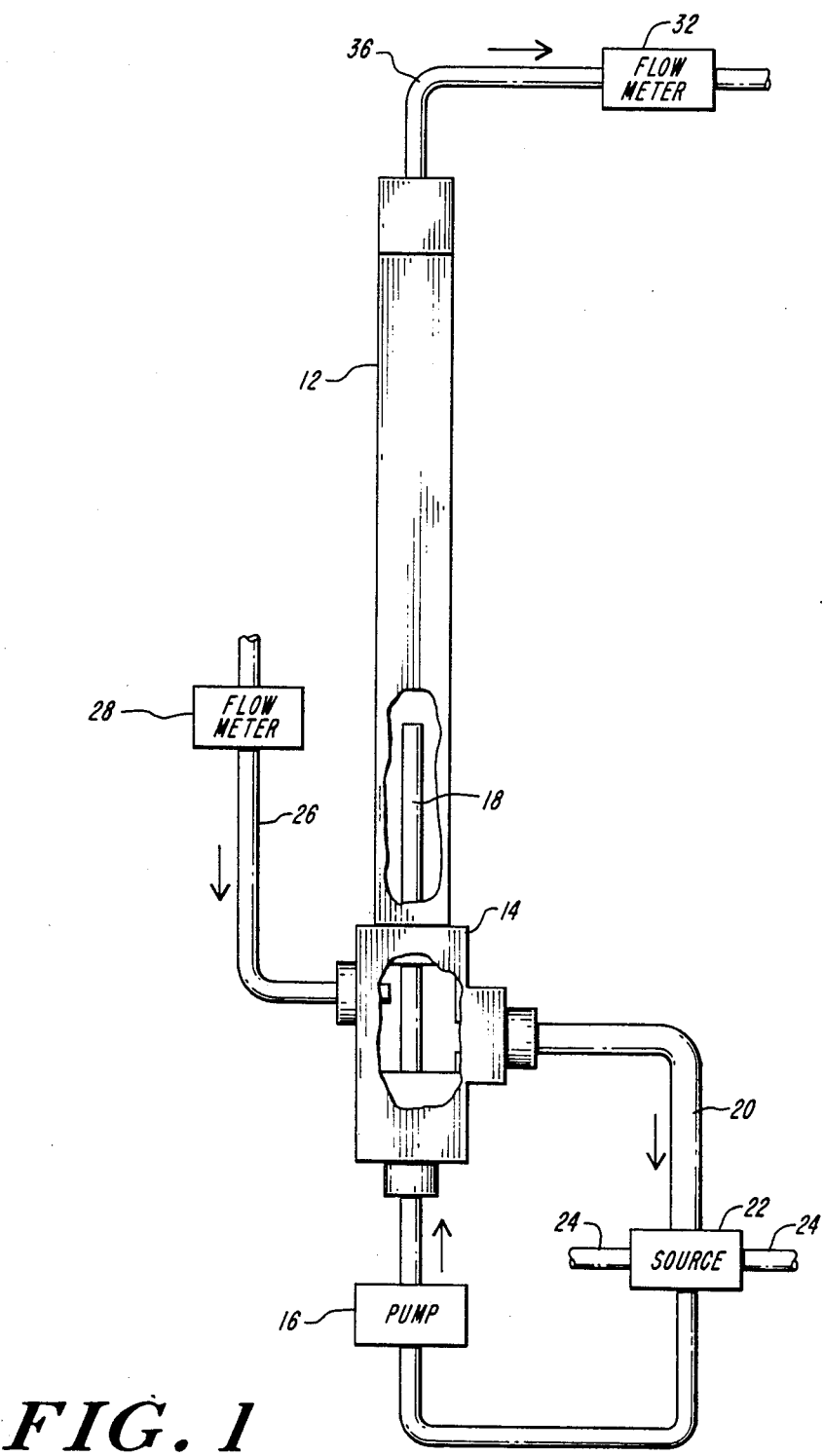
FIG. 1 is a diagram of a column for the transfer of water or other volatiles from oil to an inert gas.

The present invention contemplates a system for accurately detecting volatiles contained in an oil stream and providing increased reliability in the volatile concentration measurement by using a countercurrent flow between the cascading oil flow and an inert dry gas absorptive to the volatile. In particular, and with reference to FIG. 1, a volatile entrapment column 12 includes a bottom manifold 14 to which oil is applied from a positive displacement pump 16, capable of precisely regulated pumping rates. The oil is pumped up a standpipe 18 and flows out of the top forming a cascade down the exterior surface of the pipe 18 to collect within a reservoir of the manifold 14. From the reservoir in the manifold 14, the oil is returned via a conduit 20 to a source 22. The source 22 in conventional application to online measurement of crude oil production facilities, includes a manifold through which the crude oil passes in a conduit 24 with a portion of it cycling through the pump and conduit 20 loop, including the standpipe 18. Alternatively, and for calibration purposes, the source 22 may be a reservoir of oil having a predetermined concentration of a volatile such as water.

The column 12 includes an interior air space extending a substantial distance along the standpipe 18 through which an inert gas, such as dry nitrogen, is applied through a conduit 26 under control of a rate determining flow meter 28. The dry inert gas flows in countercurrent to the cascade of oil coming out of the top of the standpipe 18 typically a distance up to 9 inches and exhausts upward through a conduit 36 and auxiliary flow meter 32.

The counterflow concept represented by the cascade from standpipe 18 and the counterflowing inert dry gas 26 ensures a maximum exposure of the interface between the absorptive dry gas and the volatile containing oil, both of which continually refresh, ensuring that there will be always fresh, unexposed nitrogen gas in contact with volatile containing oil in which the volatile concentration remains representative of the specimen to be sampled. The flow meters 28 and 32 additionally operate to ensure a sufficient flow of nitrogen gas to avoid saturation in the nitrogen output which would impair the sensitivity and corresponding accuracy of the detection system.

Figure 2:
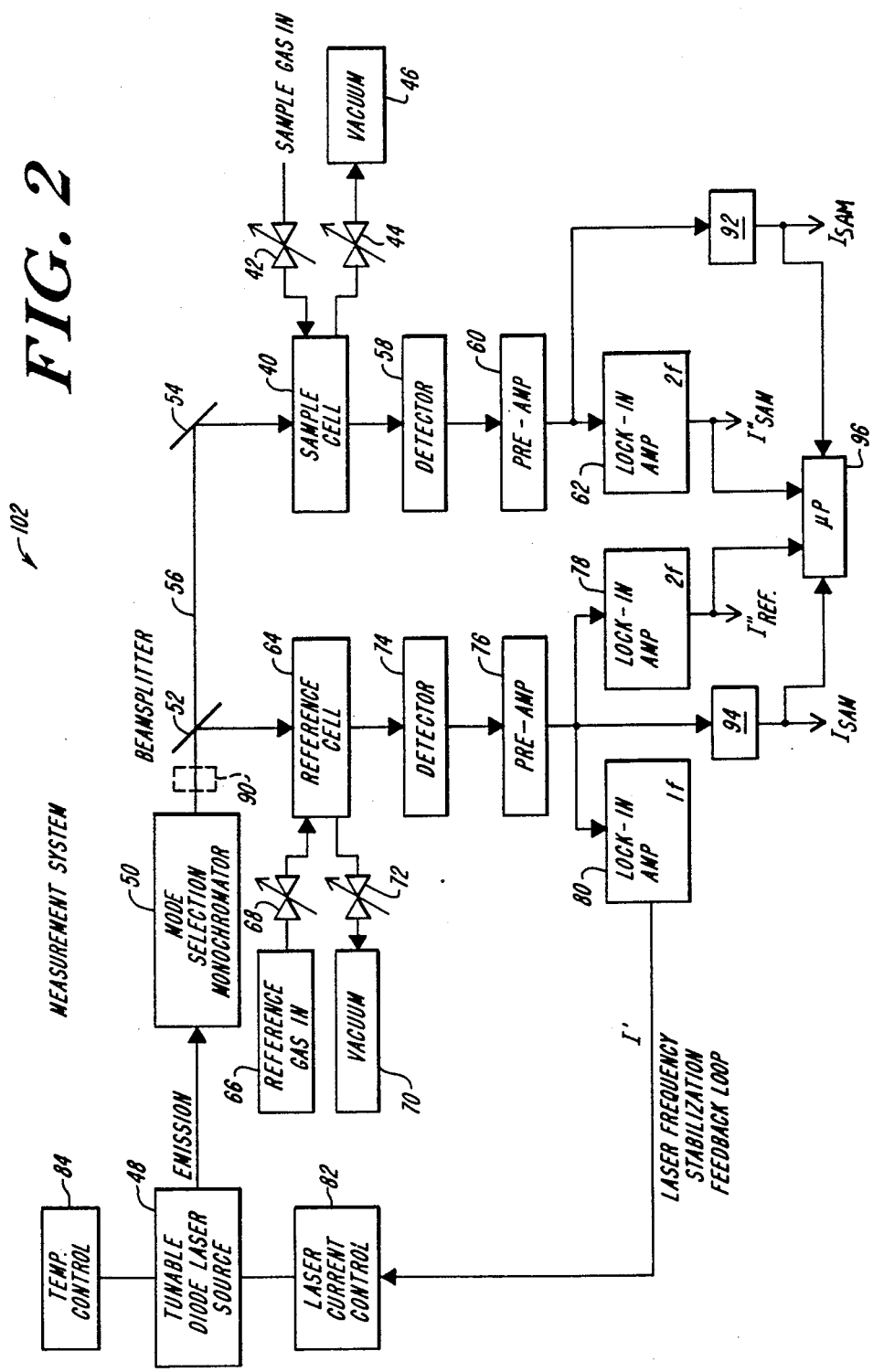
FIG. 2 is a diagram of apparatus for the measurement of water or other volatiles in an inert gas stream.

The output flow from conduit 36 and flow meter 32 is applied, in FIG. 2, through an absorption cell 40 via an input valve 42 and output valve 44 to a vacuum source 46, maintaining a consistent flow rate of the exposed and volatile containing inert gas through the sample cell 40.

Laser radiation is applied to the sample cell 40 from a tunable diode laser source 48 through a wavelength selecting monochrometer 50, beam splitter 52 and mirror 54. The beam 56 thus applied may be multiply reflected within the sample cell 40 in order to maximize the absorption of laser radiation and improve the sensitivity of the absorption cell.

The radiation is tuned in frequency to a rotational-vibrational absorption line for the volatile, typically water, being measured. The radiation in beam 56 after absorption or partial absorption in the cell 40 passes from the cell 40 to a detector 58, typically a photosensitive detector operative at the frequency of interest. The output signal from the detector is preamplified in a preamplifier 60 and applied to a lock-in amplifier 62, which effectively provides an output representative of the second derivative of the sensed intensity with respect to frequency by detecting synchronously the second harmonic of the modulation frequency of the laser radiation.

In order to calibrate the detection of absorbed volatile, the radiation in beam 56 is also applied, from beam splitter 52, through a reference absorption cell 64 which has a reference gas from a source 66 applied through a valve 68 to the cell 64 and exhausted under the pull of a vacuum 70 through an exhaust valve 72. The cell 64 may be maintained in thermal proximity to the cell 40 to avoid variations caused by thermal differences between the two cells. The radiation passing through the cell 64 and partially absorbed by the reference concentration of volatile from the source 66 is applied to a detector 74 and in turn a preamplifier 76. In the exemplary case, source 66 provides a predetermined concentration of water in nitrogen. The output of the preamplifier 76 is applied to a lock-in amplifier 78 similar to the amplifier 62 which provides second harmonic synchronous detection and thereby providing an output signal representative of the second derivative of the intensity in the beam passed through the cell 64 with respect to frequency.

The output of the preamplifier 76 is also applied through a lock-in amplifier 80 which synchronously demodulates at the first harmonic of the modulation frequency in the beam 56. Its output, representative of the first derivative of the intensity in the transmitted beam, is applied to a current control circuit 82 which controls the current applied to the diode in the source 48.

The emission frequency of the diode in the source 48 is a function of the temperature of the diode. A course control of the diode temperature is provided by a temperature controller 84 which establishes a predetermined temperature and thus emission frequency for the diode. The current used to energize the diode and activate laser emission is provided by the current controller 82 and additionally affects the laser frequency. The closed loop by which the first derivative of the intensity from the cell 64 is used to control the laser current and cause the emission frequency to center at an absorption peak for the volatile, typically water, of interest in the gas stream.

In order for the synchronous detection of the first and second harmonics to produce a signal representative of the second derivative of the intensity variation with frequency, the laser source 48 includes a modulation of the output radiation frequency, typically encompassing the half power points of the absorption curve for the volatile of interest. This modulation can typically occur at frequencies in the range between 500 Hz and 10 KHz, 6.6 KHz being preferable. Such modulation techniques are known in the art and reference is had to commonly assigned U.S. Pat. No. 4,410,273, incorporated herein by reference and commonly assigned U.S. patent application Ser. No. 07/199,241, filed May 26, 1988, specifically incorporated herein by reference. The specific theoretical underpinning with respect to the operation of the system of the present invention is more specifically described in the above-identified application. It will not be repeated here.

The second derivative outputs from the amplifier 62 and 78 may be used directly as an indication of concentration of the sample relative to the reference for indicating volatile concentration in the sampled oil stream. Alternatively, and as illustrated in the above-identified application, the ratio of the intensity to its second derivative may be formed for both sample and reference. In this case an optional chopper 90, operating at a frequency such as a few hundred Hertz, is applied in the path of the beam 56. To form signals representative of the intensity, the output of the preamplifiers 60 and 76 are applied to respective demodulators 92 and 94 which operate synchronously at the chopping frequency to provide as an output signal the difference between the output of the preamplifiers 60 and 76 between conditions when the beam is applied and blocked by the chopper 90, thereby normalizing for offsets in the detection architecture.

The outputs of the circuits 62 and 78 are applied to a microprocessor 96 along, optionally, with the outputs from the demodulators 92 and 94. The microprocessor 96 provides a correlation between the strength of the second derivative intensity signals of the sample and reference materials, or the ratio of the intensity to the second derivative for the sample and reference to provide an indication of the concentration of volatile in the oil flow. The correlation may be formed by testing a range of volatile concentrations in the oil stream as a calibration routine.

The specific measurement apparatus and technique illustrated with respect to FIG. 2 is exemplary of a preferred mechanism for detecting the concentration of the absorbed volatile in the inert gas stream. It is to be understood that other forms for detecting that concentration may be utilized within the scope of the invention. This and other modifications to the above-described exemplary system may thus be practiced within the scope of the invention which is limited only in accordance with the following claims.

I claim:

1. A method for detecting volatiles in oil comprising the steps of:
   creating a cascade of oil the presence of a volatile in which is to be detected;
   flowing a dry inert gas in countercurrent to the cascade of oil to absorb volatiles in the oil cascade in the inert gas;
   detecting radiation absorption in the inert gas after exposure to the oil cascade as an indication of volatile content of the inert gas and thus of the oil.

2. The method of claim 1 wherein said creating step includes the step of pumping the oil up and over the top of a standpipe within an enclosed column.

3. The method of claim 2 wherein said pumping step includes the step of pumping by positive displacement.

4. The method of claim 2 wherein said cascading step includes the step of cascading the oil a distance up to 9 inches past the countercurrent inert gas flow.

5. The method of claim 2 wherein said flowing step includes the step of flowing said inert gas past said cascade of oil within said column.

6. The method of claim 1 wherein said detecting step includes the step of applying the exposed inert gas to an absorption cell.

7. The method of claim 1 wherein said detecting step further includes the step of detecting the absorption of a reference, volatile containing gas to radiation and processing the absorption of the reference gas and the exposed inert gas.

8. The method of claim 1 wherein said detecting step includes the step of detecting the second derivative of the intensity of radiation passing through the volatile containing inert gas with change in frequency of radiation.

9. A system for detecting volatiles in oil comprising:
means for creating a cascade of oil the presence of a volatile in which is to be detected;
means for flowing a dry inert gas in countercurrent to the cascade of oil to absorb volatiles in the oil cascade in the inert gas;
means for detecting radiation absorption in the inert gas after exposure to the oil cascade as an indication of volatile content of the inert gas and thus of the oil.

10. The system of claim 9 wherein said creating means includes: a standpipe within an enclosed column; and means for pumping the oil up and over the top of the standpipe within the enclosed column.

11. The system of claim 10 wherein said pumping means includes a positive displacement pump.

12. The system of claim 10 wherein said cascading means includes means for cascading the oil a distance up to 9 inches past the countercurrent inert gas flow.

13. The system of claim 10 wherein said flowing means includes means for flowing said inert gas past said cascade of oil within said column.

14. The system of claim 9 wherein said detecting means includes an absorption cell for said inert gas.

15. The system of claim 9 wherein said detecting means further includes means for detecting the absorption of a reference, volatile containing gas to radiation and processing the absorption of the reference gas and the exposed inert gas.

16. The system of claim 9 wherein said detecting means includes means for detecting the second derivative of the intensity of radiation transmitted through the volatile, containing inert gas as a function of radiation frequency.

* * * * *